United States Patent [19]

Ferro et al.

[11] Patent Number: 5,120,530
[45] Date of Patent: Jun. 9, 1992

[54] ANTIMICOTIC NAIL VARNISH CONTAINING AMOROLFINE IN QUATERNARY AMMONIUM ACRYLIC COPOLYMER

[75] Inventors: Alberto Ferro, Riehen; Jürgen Gerhards, Arlesheim; Roland Werner, Basle, all of Switzerland

[73] Assignee: Hoffmann-La Roche Inc., Nutley, N.J.

[21] Appl. No.: 483,479

[22] Filed: Feb. 22, 1990

[30] Foreign Application Priority Data

Feb. 24, 1989 [CH] Switzerland ............................. 690/89
Nov. 9, 1989 [CH] Switzerland ........................... 4045/89

[51] Int. Cl.$^5$ ................... A61K 7/047; A61K 31/535; A61K 47/32
[52] U.S. Cl. ...................................... 424/61; 424/487; 523/122; 514/239.5
[58] Field of Search ............................. 424/61, 81, 487; 523/122; 524/96, 558; 514/231.2; 544/178

[56] References Cited

U.S. PATENT DOCUMENTS

| | | | |
|---|---|---|---|
| 2,677,679 | 5/1954 | Barney | 260/85.5 |
| 3,520,970 | 7/1970 | Lehmann et al. | 424/482 |
| 3,749,769 | 7/1973 | Sugiyama et al. | 424/61 |
| 4,202,894 | 5/1980 | Pfiffner | 544/178 |
| 4,425,326 | 1/1984 | Guillon et al. | 424/61 |
| 4,601,901 | 7/1986 | Guillon et al. | 424/61 |
| 4,649,045 | 3/1987 | Gaske et al. | 424/61 |
| 4,685,918 | 8/1987 | Amidon et al. | 427/2 |
| 4,857,335 | 8/1989 | Bohm | 424/440 |
| 4,957,730 | 9/1990 | Bohm et al. | 424/61 |

FOREIGN PATENT DOCUMENTS

| | | |
|---|---|---|
| 0024334 | 3/1981 | European Pat. Off. . |
| 55857 | 7/1982 | European Pat. Off. . |
| 1617751 | 4/1971 | Fed. Rep. of Germany . |
| 3112888 | 2/1982 | Fed. Rep. of Germany . |
| 3205545 | 10/1982 | Fed. Rep. of Germany . |
| 3544983 | 6/1987 | Fed. Rep. of Germany . |
| 9216-822 | 12/1984 | Japan . |
| 87/02580 | 5/1987 | PCT Int'l Appl. . |
| 298271 | 1/1989 | PCT Int'l Appl. . |
| 2107186 | 4/1983 | United Kingdom . |
| 2188844 | 10/1987 | United Kingdom . |
| 2202743 | 10/1988 | United Kingdom . |

OTHER PUBLICATIONS

Med. Report No. 4/vol. 12, Berlin, Jul. 1988.
Prospectus, Eudragit ® RL and RS Anwendung in der Arzneimittelherstellung.
Chem. Abs. 108, No. 10,820992 (abstract of Japanese Patent Publication (Kokai) No. 123112/1987).
Chem. Abs. 110, No. 14,121426S (abstract of Japanese Patent Application (Kokai) No. 130541/1988).
Polak et al., "Antifungal Activity of Amorolfine in vitro and in vivo". Recent trends in the Discovery Development and Evaluation of Antifungal Agents. R. A., Fromtling (ED) 1987. J. R. Prous Science Publischers, S.A.

Primary Examiner—Thurman K. Page
Assistant Examiner—E. J. Webman
Attorney, Agent, or Firm—George M. Gould; William G. Isgro; William Krovatin

[57] ABSTRACT

An antimycotically-active nail varnish, which contains an antimycotically-active substance selected from 4-[3-[p-(α,α-dimethyl-benzyl)-phenyl]-2-methyl-propyl]-2,6-dimethylmorpholine, 4-[-[p-(1,1,-dimethylpropyl)-phenyl]-2-methyl-propyl]-2,6-dimethyl-morpholine and salts thereof and a water-insoluble film former which a copolymerizate of acrylic acid esters and methacrylic acid esters having a low content of quaternary ammonium groups, is described.

22 Claims, No Drawings

ANTIMICOTIC NAIL VARNISH CONTAINING AMOROLFINE IN QUATERNARY AMMONIUM ACRYLIC COPOLYMER

BRIEF SUMMARY OF THE INVENTION

The invention relates to an antimycotically-active preparation or composition in the form of a nail varnish, which contains at least one antimycotically-active substance and at least one water-insoluble film-former. The invention also relates to a process for the manufacture of such a composition.

This object is achieved in accordance with the invention by using as the water-insoluble film-former a copolymerizate of acrylic acid esters and methacrylic acid esters having a low content of quaternary ammonium groups.

DETAILED DESCRIPTION OF THE INVENTION

The invention relates to an antimycotically-active preparation or composition in the form of a nail varnish, which contains at least one antimycotically-active substance and at least one water-insoluble film-former. The invention also relates to a process for the manufacture of such a composition.

The object of the invention is to improve the quality of compositions of the kind referred to above, especially with respect to the following properties: good rate of penetration, good skin compatibility, good flow behaviour, good spreadability, short drying time, only moderately high gloss, sufficiently great hardness and long durability (about 3-4 days).

This object is achieved in accordance with the invention by using as the water-insoluble film-former a copolymerizate of acrylic acid esters and methacrylic acid esters having a low content of quaternary ammonium groups. Such copolymerizates are disclosed e.g. in U.S. Pat. No. 2,677,679 and DAS No. 1,617,751.

Preferably, the content of quaternary ammonium groups in the copolymerizate is such that the molar ratio of ammonium groups to the remaining neutral acrylic acid esters lies between about 1:20 and about 1:40. The molar ratio of ammonium groups to the methacrylic acid esters (not containing ammonium groups) preferably also lies between about 1:20 and about 1:40.

The average molecular weight of such a copolymerizate can be about 150,000. Such copolymerizates can be characterized by the following partial formula in which $R_1$ is hydrogen or methyl and $R_2$ is methyl or ethyl

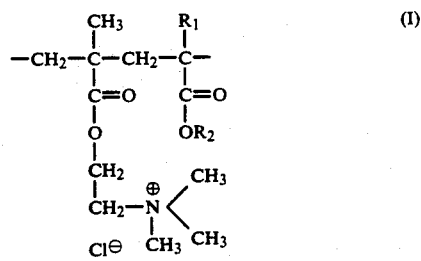

Such substances are commercially available as 12.5% varnish solutions and as solvent-free solids under the brand EUDRAGIT® RL and RS (see Römpp's Chemielexikon, 8th edition, p. 1211).

Such substances can also be mixed with one another according to the particular requirements.

Because of their swelling capacity and porosity, the use of such copolymerizates guarantees a high rate of diffusion and a high rate of permeability for the active substance.

Further, the use of such copolymerizates guarantees, in addition to the aforementioned properties, a high resistance of the coating of varnish against mechanical damage and against washing-off in the entire pH range. This makes it possible for the film of varnish containing the antimycotically-active substance to remain on the nail for several days and therefore the period between two applications of the varnish solution can be as long as several days.

Conveniently, in a composition in accordance with the invention the copolymerizate and the antimycotically-active substance and any further additives such as plasticizers, evaporation retarders and/or evaporation accelerators are dissolved in an inert organic solvent, preferably in ethanol or methylene chloride.

As plasticizers there can be named: glycerol acetates such as triacetin, phthalates or plasticizers based on camphor. In addition to the preferred solvents, namely ethanol and methylene chloride, there can also be used, for example, acetone and isopropanol.

Toluene, butanol, butyl acetate, amyl alcohol and amyl acetate are examples of evaporation retarders and ethyl acetate can be named as an example of an evaporation accelerator.

The antimycotically-active substance which is present in the preparation in accordance with the invention can be 4-[3-[p-(α,α-dimethyl-benzyl)-phenyl]-2-methylpropyl]-2,6-dimethyl-morpholine or 4-[3-[p-(1,1-dimethylpropyl)-phenyl]-2-methylpropyl]-2,6-dimethylmorpholine in the form of a salt, especially in the form of the hydrochloride or the nitrate. The cis isomers of these compounds are preferably used. These cis isomers are known from European Patent Publication No. 24 334. In this publication, the second-named compound just above, is disclosed under the nomenclature 4-[3-(p-tert.amyl-phenyl)-2-methylpropyl]-2,6-dimethylmorpholine. The use of the cis isomer of this compound, especially in the form of the hydrochloride, is particularly preferred.

An especially preferred embodiment of a composition in accordance with the invention contains the antimycotically-active substance, especially the aforementioned morpholine derivative, in an amount of about 0.25 to about 10 wt. %, especially in an amount of about 5 wt. %, calculated as morpholine base.

In accordance with a preferred embodiment of a composition of the invention, the composition contains the water-insoluble copolymerizate in an amount of about 2-30 wt. %, preferably 10-20 wt. %, especially about 12.5 wt. %.

The process in accordance with the invention for the preparation of a composition comprises mixing the copolymerizate in dissolved form with the active substance and any additives such as plasticizers, evaporation accelerators, evaporation retarders and the like.

EXAMPLE 1

A composition in accordance with the invention, which contains methylene chloride as the solvent, has the following composition:

| | |
|---|---|
| Active substance | 5.574 g |
| EUDRAGIT ® RL 100 | 12.5 g |
| Triacetin | 2.5 g |
| Butyl acetate | 15.0 g |
| Methylene chloride | ad 100.0 ml |

EXAMPLE 2

A composition in accordance with the invention, which contains ethanol as the solvent, has the following composition:

| | |
|---|---|
| Active substance | 5.574 g |
| EUDRAGIT ® RL 100 | 12.5 g |
| Butyl acetate | 5.0 g |
| Ethyl acetate | 15.0 g |
| Ethanol | ad 100.0 ml |

The active substance used in the above Examples was cis-4-[3-[p-(1,1-dimethylpropyl)-phenyl]-2-methyl-propyl]-2,6-dimethyl-morpholine hydrochloride and EUDRAGIT ® RL 100 is a copolymerizate of acrylic acid esters and methacrylic acid esters which contains ammonium groups in a molar ratio of 1:20 (see the company prospectus of Röhm Pharma GMBH, Weiterstadt, Federal Republic of Germany: "EUDRAGIT ® RL und RS Anwendung in der Arzneimittelherstellung" 1982). Instead of this particular copolymerizate, structurally similar copolymerizates can be used, e.g. a copolymerizate of trimethylmethacryloxyethylammonium chloride, methyl methacrylate, and ethyl acrylate, having a low content of ammonium groups.

In the above Examples cis-4-[3-[p-($\alpha,\alpha$-dimethyl-benzyl)-phenyl]-2-methyl-propyl]-2,6-dimethyl-morpholine hydrochloride may alternatively be used as the active substance.

We claim:

1. A nail varnish composition comprising about 0.25–10 wt. % of a antimycotically-active substance and about 2–30 wt. % of a water-soluble film-former, wherein the antimycotically-active substance is selected from the group consisting of 4-[3-[p-($\alpha,\alpha$-dimethyl-benzyl)-phenyl]-2-methyl-propyl]-2,6-dimethylmorpholine, 4-[3-[p-(1,1-dimethylpropyl)-phenyl]-2-methyl-propyl]-2,6-dimethyl-morpholine and salts thereof, and the water-insoluble film-former is a copolymerizate of acrylic acid esters and methacrylic acid esters having a low content of quaternary ammonium groups, the molar ratio of such ammonium groups to neutral acrylic acid ester units being between about 1:20 and about 1:40, and the molar ratio of such ammonium groups to those methacrylic acid ester units not featuring quaternary ammonium groups is between about 1:20 and about 1:40.

2. A composition according to claim 1, wherein the average molecular weight of the copolymerizate is about 150,000.

3. A composition according to claim 2 which further comprises a plasticizer, an evaporation retarder and an evaporation accelerator.

4. A composition according to claim 3, wherein the copolymerizate, the antimycotically-active substance, the plasticizer, the evaporation retarder, and the evaporation accelerator are dissolved in an inert organic solvent.

5. A composition in accordance with claim 4, wherein the inert organic solvent is ethanol or methylene chloride.

6. A process for the preparation of a composition of claim 3, which comprises mixing the copolymerizate in dissolved form with the antimycotically-active substance, a plasticizer, an evaporation retarder, and an evaporation accelerator.

7. A composition according to claim 1, wherein the antimycotically-active substance is 4-[3-[p-($\alpha,\alpha$-dimethyl-benzyl)-phenyl]-2-methyl-propyl]-2,6-dimethylmorpholine, or a salt thereof.

8. A composition according to claim 7, wherein the salt is the hydrochloride.

9. A composition according to claim 7, wherein the antimycotically-active substance is the cis-isomer.

10. A composition according to claim 1, wherein the antimycotically-active substance is 4-[3-[p-(1,1-dimethylpropyl)-phenyl]-2-methyl-propyl]-2,6-dimethyl-morpholine, or a salt thereof.

11. A composition according to claim 10, wherein the salt is the hydrochloride.

12. A composition according to claim 10, wherein the antimycotically-active substance is the cis-isomer.

13. A composition according to claim 1, wherein the antimycotically-active substance is present in an amount of about 5 wt. %.

14. A composition according to claim 1, wherein the water-insoluble copolymerizate is present in an amount of about 10–20 wt. %.

15. A composition according to claim 14, wherein the water-insoluble copolymerizate is present in an amount of about 12.5 wt. %.

16. A process for the preparation of a nail varnish composition of claim 1, which comprises mixing the copolymerizate in dissolved form with the antimycotically-active substance.

17. A process according to claim 16, wherein the average molecular weight of the copolymerizate is about 150,000.

18. A process according to claim 16, wherein the antimycotically-active substance is 4-[3-[p-($\alpha,\alpha$-dimethyl-benzyl)-phenyl]-2-methyl-propyl]-2,6-dimethyl-morpholine, or the hydrochloride salt thereof.

19. A process according to claim 16, wherein the antimycotically-active substance is 4-[3-[p-(1,1-dimethylpropyl)-phenyl]-2-methylpropyl]-2,6-dimethylmorpholine, or the hydrochloride salt thereof.

20. A process according to claim 16, wherein the antimycotically-active substance is present in an amount of about 5 wt. %.

21. A process according to claim 16, wherein the copolymerizate is present in an amount of about 10–20 wt. %.

22. A process according to claim 21, wherein the copolymerizate is present in an amount of about 12.5 wt. %.

* * * * *

UNITED STATES PATENT AND TRADEMARK OFFICE
CERTIFICATE OF CORRECTION

PATENT NO. : 5,120,530
DATED : June 9, 1992
INVENTOR(S) : Alberto Ferro, Jurgen Gerhards, Roland Werner It is certified that error appears in the above-identified patent and that said Letters Patent is hereby corrected as shown below:

- In Claim 1, Column 3, line 42: "water-soluble film-former" should read --- water-insoluble film former- --- .

Signed and Sealed this

Thirteenth Day of June, 1995

Attest:

BRUCE LEHMAN

Attesting Officer    Commissioner of Patents and Trademarks